United States Patent
Kotanko et al.

(10) Patent No.: US 11,623,032 B2
(45) Date of Patent: Apr. 11, 2023

(54) TECHNIQUES FOR DETERMINING PATIENT BLOOD CHARACTERISTICS DURING A DIALYSIS PROCESS

(71) Applicant: Fresenius Medical Care Holdings, Inc., Waltham, MA (US)

(72) Inventors: Peter Kotanko, New York, NY (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 333 days.

(21) Appl. No.: 17/061,910

(22) Filed: Oct. 2, 2020

(65) Prior Publication Data
US 2021/0100945 A1   Apr. 8, 2021

Related U.S. Application Data

(60) Provisional application No. 62/910,739, filed on Oct. 4, 2019.

(51) Int. Cl.
*A61M 1/36* (2006.01)
*A61M 1/34* (2006.01)
*A61M 1/16* (2006.01)

(52) U.S. Cl.
CPC ............ *A61M 1/3644* (2014.02); *A61M 1/16* (2013.01); *A61M 1/341* (2014.02);
(Continued)

(58) Field of Classification Search
CPC ...... A61M 1/16; A61M 1/361; A61M 1/3644; A61M 1/3646; A61M 1/341;
(Continued)

(56) References Cited

U.S. PATENT DOCUMENTS

| 5,932,103 A | 8/1999 | Kenley et al. |
| 7,170,591 B2 | 1/2007 | Ohishi et al. |

(Continued)

FOREIGN PATENT DOCUMENTS

| EP | 1872811 B1 | 4/2011 |
| EP | 2583700 A1 | 4/2013 |

(Continued)

OTHER PUBLICATIONS

International Search Report and Written Opinion for International application No. PCT/US2020/053955, dated Feb. 16, 2021, 12 pages.

(Continued)

*Primary Examiner* — John Kim
(74) *Attorney, Agent, or Firm* — KDW Firm PLLC

(57) ABSTRACT

Techniques and apparatus for de-priming processes are described. For example, in one embodiment, an apparatus may include at least one processor and a memory coupled to the at least one processor, the memory may include instructions that, when executed by the processor, may cause the at least one processor to determine a priming volume of a primer fluid infused into a priming system associated with the patient during a priming phase of the dialysis treatment, cause an ultrafiltration rate of an ultrafiltration pump of the dialysis machine in fluid communication with the patient to be changed from a treatment ultrafiltration rate to a de-priming ultrafiltration rate to remove the priming volume over a de-priming time period, and cause, after the de-priming time period, the ultrafiltration rate of the ultrafiltration pump to be changed back the treatment ultrafiltration rate. Other embodiments are described.

23 Claims, 7 Drawing Sheets

(52) U.S. Cl.
CPC .......... *A61M 1/3413* (2013.01); *A61M 1/361* (2014.02); *A61M 1/3646* (2014.02); *A61M 2205/3334* (2013.01); *A61M 2205/50* (2013.01); *A61M 2205/52* (2013.01); *A61M 2230/20* (2013.01); *A61M 2230/207* (2013.01)

(58) Field of Classification Search
CPC ........ A61M 1/3413; A61M 2205/3334; A61M 2205/52; A61M 2230/20; A61M 2230/207; A61M 2205/50
See application file for complete search history.

(56) References Cited

U.S. PATENT DOCUMENTS

2013/0144139 A1 6/2013 Zhang et al.
2016/0169861 A1 6/2016 Chamney et al.

FOREIGN PATENT DOCUMENTS

| | | |
|---|---|---|
| EP | 3033704 A1 | 6/2016 |
| WO | 2015026542 A1 | 2/2015 |
| WO | 2015179401 A1 | 11/2015 |
| WO | 2015179523 A1 | 11/2015 |

OTHER PUBLICATIONS

Garro, R., et al., "CRIT-LINE: a noninvasive tool to monitor hemoglobin levels in pediatric hemodialysis patients", Pediatric Nephrology 30:991-998 (2015). Abstract.
Eschbach, J.W., and Adamson, J.W., "Anemia of end-stage renal disease (ESRD)", Kidney Int 28:1-5 (1985). Abstract.
Thwin, O., et al., "Estimation of pre-dialysis hemoglobin concentration using intradialytic Crit-Line Monitor readings", ASN Kidney Week 2018, Hgb Study Poster from Renatl Research Institute.

TECHNIQUES FOR DETERMINING PATIENT BLOOD CHARACTERISTICS DURING A DIALYSIS PROCESS

CROSS-REFERENCE TO RELATED APPLICATION

This application claims the benefit of priority of 35 U.S.C. § 119(e) to U.S. Provisional Patent Application Ser. No. 62/910,739, filed on Oct. 4, 2019, which is incorporated by reference in its entirety as if fully set forth herein.

FIELD

The disclosure generally relates to a dialysis system, and more particularly to techniques for determining values of patient blood characteristics during a dialysis treatment.

BACKGROUND

Dialysis patients may experience various complications over the course of treatment. For example, anemia can be a major complication experienced by dialysis patients, particularly patients with end-stage kidney disease. Accordingly, healthcare professionals routinely obtain blood tests before and during dialysis treatment to monitor for such complications, such as an anemic condition. For instance, hemoglobin (Hgb) levels may be monitored because to detect anemia. Conventional examination procedures typically involve periodic blood draws, such as weekly blood draws. However, these periodic blood draws create extra costs, are logistically difficult for healthcare providers, and take time to process before results can be available. For instance, the blood samples are typically sent to a lab, where pre-treatment Hgb levels are measured. While the results of these measurements are useful in guiding therapy, it may take days until they are communicated back to the dialysis provider.

Blood monitoring devices may be used during dialysis treatment to determine patient Hgb levels. However, during certain portions of dialysis treatment, the patient's blood may be diluted or otherwise different from normal conditions, leading to a pre-dialysis Hgb measurement that doesn't reflect the patient's actual Hgb concentration. For example, during hemodialysis (HD), the initial Hgb values obtained after the start of HD are systematically lower than corresponding pre-HD values due to hemodilution caused by infusion of the priming fluid that occurs during the start of HD.

Accordingly, conventional systems are not capable of providing accurate and efficient pre-dialysis measurements of patient blood characteristics that are required to fully evaluate dialysis patients for anemia, for example, to appropriately assess the degree of anemia as reflected by pre-dialysis Hgb concentration, which is the parameter used for anemia management in clinical practice.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with various embodiments of the present disclosure is an apparatus that may include at least one memory and logic coupled to the at least one memory to perform a de-priming process of a patient undergoing a dialysis treatment via a dialysis machine operably coupled to the apparatus. The logic may operate to determine a priming volume of a primer fluid infused into a priming system associated with the patient during a priming phase of the dialysis treatment, cause an ultrafiltration rate of an ultrafiltration pump of the dialysis machine to be changed from a treatment ultrafiltration rate to a de-priming ultrafiltration rate to remove the priming volume over a de-priming time period, and cause, after the de-priming time period, the ultrafiltration rate of the ultrafiltration pump to be changed back to the treatment ultrafiltration rate.

In some embodiments of the apparatus, the logic may operate to measure a blood characteristic after the de-priming period, the blood characteristic comprising at least one of a hematocrit level or a hemoglobin (Hgb) level.

In various embodiments of the apparatus, the de-priming ultrafiltration rate may include about 2000 ml/hour to about 4000 ml/hour. In some embodiments of the apparatus, the de-priming time period may include about 6 minutes to about 10 minutes. In various embodiments of the apparatus, the de-priming ultrafiltration rate may include about 3000 ml/hour and the de-priming time period comprising about 6 minutes.

In exemplary embodiments of the apparatus, the logic may operate to determine a de-priming start time for setting the ultrafiltration rate, the de-priming start time comprising a start time of the dialysis treatment.

In some embodiments of the apparatus, the logic may operate to determine the priming volume based on a dialyzer volume and a tubing set volume. In various embodiments of the apparatus, the logic may operate to determine the de-priming ultrafiltration rate based on a target blood flow rate. In some embodiments of the apparatus, the target blood flow rate may include about 150 ml/min to about 250 ml/min. In exemplary embodiments of the apparatus, the logic may operate to determine the de-priming ultrafiltration rate to remove the priming volume within the de-priming time period.

In accordance with various embodiments of the present disclosure is a method of performing a de-priming process. The method may include via a processor of a computing device operably coupled to a dialysis machine performing a dialysis process on a patient: determining a priming volume of a primer fluid infused into a priming system associated with the patient during a priming phase of the dialysis treatment, causing an ultrafiltration rate of an ultrafiltration pump of the dialysis machine to be changed from a treatment ultrafiltration rate to a de-priming ultrafiltration rate to remove the priming volume over a de-priming time period, and causing, after the de-priming time period, the ultrafiltration rate of the ultrafiltration pump to be changed back to the treatment ultrafiltration rate.

In some embodiments of the method, the method may include measuring a blood characteristic after the de-priming period, the blood characteristic comprising at least one of a hematocrit level or a hemoglobin (Hgb) level.

In various embodiments of the method, the de-priming ultrafiltration rate may include about 2000 ml/hour to about 4000 ml/hour. In some embodiments of the method, the de-priming time period may include about 6 minutes to about 10 minutes. In various embodiments of the method, the de-priming ultrafiltration rate may include about 3000 ml/hour and the de-priming time period comprising about 6 minutes.

In exemplary embodiments of the method, the method may include determining a de-priming start time for setting the ultrafiltration rate, the de-priming start time comprising a start time of the dialysis treatment.

In some embodiments of the method, the method may include determining the priming volume based on a dialysis machine volume and a tubing set volume. In various embodiments of the method, the method may include determining the de-priming ultrafiltration based on a target blood flow rate. In some embodiments of the method, the target blood flow rate may include about 150 ml/min to about 250 ml/min.

In various embodiments of the method, the method may include determining the de-priming ultrafiltration rate to remove the priming volume within the de-priming time period.

BRIEF DESCRIPTION OF THE DRAWINGS

By way of example, specific embodiments of the disclosed machine will now be described, with reference to the accompanying drawings, in which.

DETAILED DESCRIPTION

Figure 1:
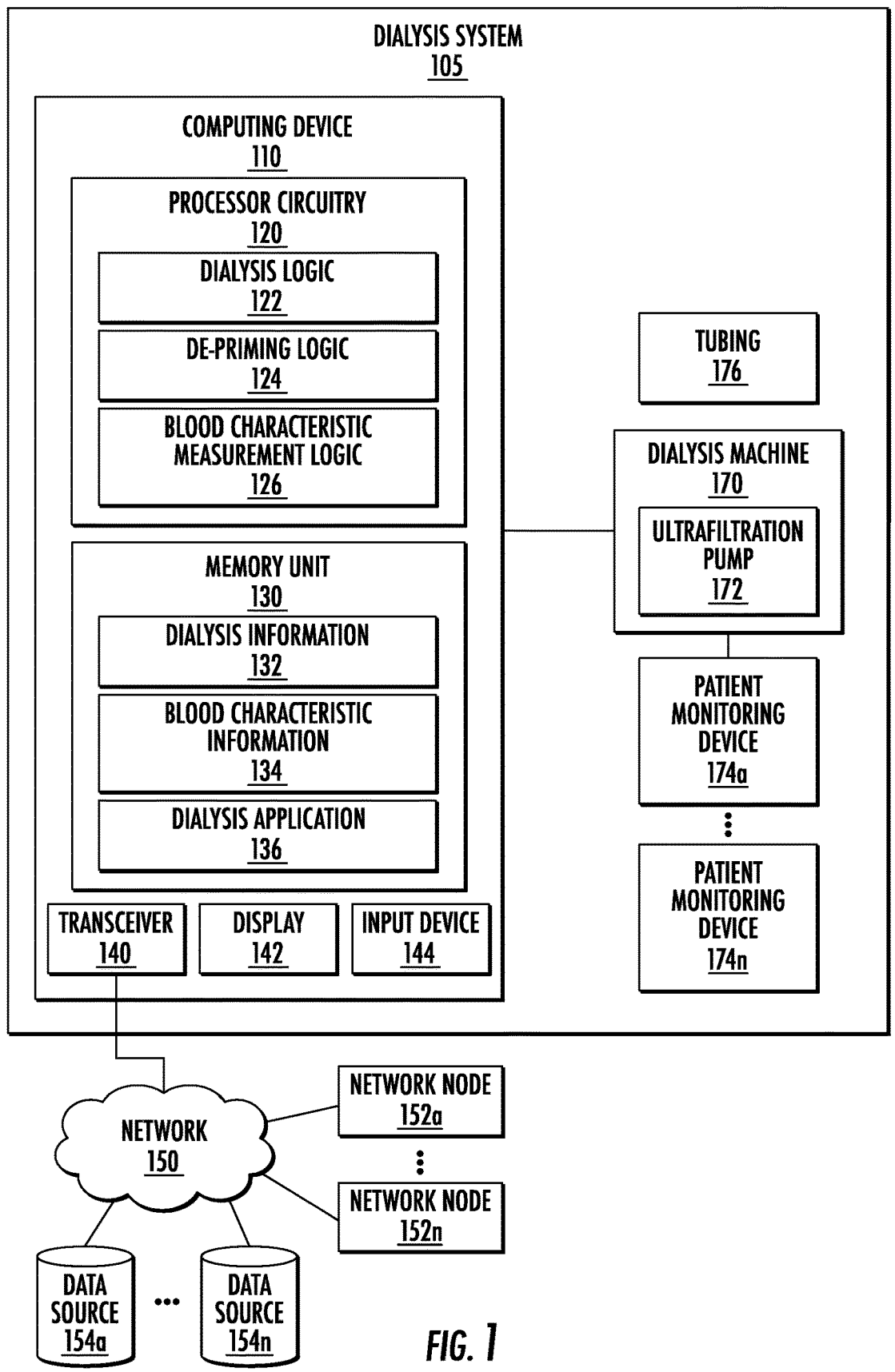
FIG. 1 illustrates a first exemplary operating environment in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Blood is routinely drawn from dialysis patients for testing before dialysis to monitor patient health and to detect and/or monitor complications, such as anemia. For example, blood samples may be drawn after cannulation of the patient but before the patient is connected to the dialysis machine. These blood samples may be sent to a lab for processing. However, the results typically take days to be returned to the healthcare provider. Devices are now available to measure certain properties of patient blood during dialysis by taking measurements of blood flowing through the extracorporeal circuit of a dialysis system. For example, the Crit-Line® Monitor (CLM), available from Fresenius Medical Care Waltham, Mass., United States of America, may measure patient hematocrit (which may be used to determine hemoglobin (Hgb) levels) and/or relative blood volume (RBV) information during dialysis. In another example, the CLiC device available from Fresenius Medical Care, Waltham, Mass., United States of America may measure absolute hematocrit, RBV, and continuous oxygen saturation. Accordingly, certain patient blood characteristics may be monitored during a dialysis treatment.

A dialysis system typically undergoes a priming process or phase prior to the start of dialysis treatment of the patient. In general, the priming phase may operate to remove air, debris, chemicals, and/or the like from the dialysis machine and associated tubing. During hemodialysis (HD), the extracorporeal circuit and/or the patient blood circuit may be primed with a priming fluid, such as a saline solution. Accordingly, a volume of priming fluid (or priming volume) may be circulated through the extracorporeal circuit and the patient blood circuit during the start of dialysis.

An effect of the priming phase (i.e., a phase during infusion of the priming fluid into the patient's blood stream) is that patient blood flowing through the extracorporeal circuit may be diluted by the priming fluid for an initial period at the start of dialysis. Accordingly, devices, such as a CLiC device, that measure blood characteristics as the blood is flowing through the extracorporeal circuit may be measuring diluted blood, leading to erroneous measurements (or, more specifically, measurements that are not reflective of the actual pre-dialysis blood characteristics). For example, Hgb values measured via a CLM device during the start of dialysis (i.e., within the first 1 minute to 10 minutes) may be lower than corresponding laboratory results (for example, about 0.5 g/dL lower) due to hemodilution of the patient blood. Therefore, although CLM and CliC devices are capable of determining Hgb concentration during a dialysis treatment, however, the pre-dialysis measurements may be systematically inaccurate due to hemodilution of patient blood. Accordingly, using conventional technology, the CLM and/or CLiC measurements in the first few minutes (i.e., when the patient's blood may be diluted with priming fluid) of a dialysis treatment may not be an appropriate substitute for a lab-based pre-dialysis Hgb measurement.

Accordingly, some embodiments may provide a de-priming process operative to de-prime patient blood to allow for measurement of non-diluted blood characteristics via a blood characteristic measurement device. In some embodiments, the de-priming process may de-prime a priming system which may include a portion of the patient vasculature, tubing (including, for example, an extracorporeal circuit), a dialysis machine, and/or any other components that may have been infused with priming fluid. In some embodiments, the priming system may be or may include an extracorporeal circuit used during the dialysis treatment. The de-priming process may operate to provide de-primed patient blood having characteristics that are the same or substantially similar to patient pre-dialysis blood. In this manner, a quasi-pre-dialysis blood sample may be taken after dialysis (or at least the priming phase of dialysis) has begun.

In order to use the CLiC, CLM, or other device for approximation of the patient's pre-HD hematocrit, the patient's blood must be returned as near as possible to its pre-treatment hematocrit state. Since the first minute or so of treatment involves pumping a known amount (for instance, 240 mL) of saline into the patient, some embodiments may include a de-priming process during an initial phase of treatment to involve vigorous ultrafiltration, for example, enough to remove a volume of fluid equal to the amount of primer fluid introduced into the patient. The de-priming process may operate rapidly, to minimize the possibility that the saline migrates beyond the vascular compartment. In some embodiments, the de-priming process may be performed at a relatively low blood flow rate, for example, to minimize secondary effects such as saline trapping due to vascular access recirculation. After removing an amount of plasma water equal to the priming volume or another volume sufficient to de-prime the patient, the patient's extracorporeal blood approximates, to a useful degree, the pre-treatment hematocrit state. After completion of the de-priming process, a CLiC, CLM, or other device can provide a Hgb measurement, for example, a quasi-pre-dialysis Hgb concentration measurement, that would otherwise have to come from a laboratory.

Accordingly, some embodiments may include technical features which provide technological advantages over conventional systems, including improvements in computing technology (for instance, computing systems operative to control or otherwise manage dialysis systems). One non-limiting example of a technological advantage is allowing real-time blood characteristic measurement devices, such as a CliC and/or CLM device, to measure accurate pre-HD blood characteristics, for example, that would be sufficiently close to laboratory results to be useful for monitoring patient health (for instance, an anemic condition). Another non-limiting example of a technological advantage is operating a de-priming process using a high initial ultrafiltration rate (UFR) and low blood flow rate that allows for rapid removal of the infused saline volume while limiting the potential impact of unknowns associated with saline extravasation and vascular refill. A further non-limiting example of a technological advantage may include improvements in computing technology for dialysis systems and/or computing devices operating or otherwise interacting with dialysis systems that allow such devices and systems to perform a de-priming process according to some embodiments, which is not possible with conventional computing technology and/or dialysis systems.

In addition, some embodiments may include technical features that are integrated into a practical application. For example, embodiments may include technical features (e.g., processes, algorithms, devices, apparatuses, and/or the like) that are integrated into a dialysis system and/or process. For instance, some embodiments may include a de-priming process integrated into a dialysis system for performing dialysis on a patient. A dialysis system configured according to some embodiments may be better able to allow for accurate, efficient patient blood testing, including testing of pre-dialysis blood characteristics, during a dialysis process compared with conventional systems. In one practical application, the patient blood testing may be used to determine a diagnosis, administer a treatment (e.g., a drug treatment, a dialysis treatment, and/or the like) to a patient, and/or the like. In another instance, a de-priming process according to some embodiments may be integrated into the practical application of controlling portions of a dialysis system, such as a filtration system, including, without limitation, an ultrafiltration pump to remove priming fluid. In some embodiments, a de-priming process may be integrated into the practical application of removing or substantially removing a volume of priming fluid from a patient and associated components (for instance, tubing, dialysis machine, extracorporeal circuit, and/or the like) within a de-priming time period. Technical features of some embodiments may be integrated into other practical applications, as would be known to those of skill in the art.

FIG. 1 illustrates an example of an operating environment 100 that may be representative of some embodiments. As shown in FIG. 1, operating environment 100 may include a dialysis system 105 associated with a dialysis machine 170. In some embodiments, dialysis machine 170 may include, may be operably coupled to, or otherwise associated with various components, such as an ultrafiltration (UF) pump 172, patient monitoring devices 174a-n, and/or tubing 176 (for instance, tubing of an extracorporeal circuit). In some embodiments, dialysis machine may be or may include a dialyzer (not shown). In some embodiments, patient monitoring devices 174a-n may include devices operative to measure or otherwise determine patient blood characteristics, including, without limitation, hematocrit, Hgb, oxygen saturation, blood pressure, and/or the like. In various embodiments, patient monitoring devices 174a-n may include a CLM device, a CLiC device, and/or the like. In some embodiments, one or more of patient monitoring devices 174a-n may be operably coupled to dialysis machine 170, components of dialysis machine 170, tubing 176, and/or a patient 178. Embodiments are not limited in this context.

In various embodiments, dialysis machine 170 may be or may include an HD dialysis system. For example, dialysis machine 170 may be or may include a Fresenius 2008T HD machine available from Fresenius Medical Care, Waltham, Mass., United States of America. Although HD is used in examples in this Detailed Description, embodiments are not so limited, as other types of dialysis systems and treatments capable of being performed according to some embodiments are contemplated herein.

In various embodiments, dialysis system 105 may include a computing device 110 communicatively coupled to dialysis machine 170 and/or components associated with dialysis machine 170. Computing device 110 may be configured to manage, among other things, operational aspects of dialysis machine 170 to perform a dialysis treatment on a patient. Although only one computing device 110 and dialysis machine 170 are depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via a network 150 (i.e., network nodes 152a-n). A single computing device 110 and dialysis machine 170 are depicted for illustrative purposes only to simplify the figure. For example, computing device 110 may operate to partially or wholly operate a dialysis process for a plurality of dialysis machines 170 coupled to computing device 110, for instance, via network 150. Embodiments are not limited in this context.

Computing device 110 may include a transceiver 140, a display 142, an input device, 144, and/or processor circuitry 120 that may be communicatively coupled to a memory unit 130. Processor circuitry 120 may be, may include, and/or may access various logics for performing processes according to some embodiments. For instance, processor circuitry 120 may include and/or may access a dialysis logic 122, de-priming logic 124, and/or blood characteristic measurement logic 126. Processing circuitry 120, dialysis logic 122, de-priming logic 124, blood characteristic measurement logic 126 and/or portions thereof, may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 700. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a proportional-integral-derivative (PID) controller, combinations of any of the foregoing, and/or the like.

Although dialysis logic 122, de-priming logic 124, and blood characteristic measurement logic 126 are depicted in FIG. 1 as being within processor circuitry 120, embodiments are not so limited. For example, dialysis logic 122, de-priming logic 124, blood characteristic measurement logic 126, and/or any component thereof, may be located within an accelerator, a processor core, an interface, an individual processor die, implemented entirely as a software application (for instance, a dialysis application 136) and/or the like. In some embodiments, computing device 110 and/or components thereof may be an embedded or integral component of dialysis machine. For instance, processor circuitry 120, dialysis logic 122, de-priming logic 124, blood characteristic measurement logic 126, and/or portions thereof may be arranged in or otherwise integral to dialysis machine 170.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store dialysis information 132 and/or blood characteristic information 134. In some embodiments, dialysis information 132 may include information generated associated with a dialysis process, including dialysis machine 170 operational information, patient information, and/or priming information. Operational information may include a UFR, a UF goal (UFG), treatment time, operating parameters, and/or the like of a dialysis process. Patient information may include body temperature, heart rate, relative blood volume (RBV), oxygen saturation, blood pressure, intradialytic hypotension (IDH) information (for instance, predicted IDH information), and/or the like. Priming information may include information associated with a priming phase of dialysis machine 170. Non-limiting examples of priming information may include a priming duration and/or volume information used, for example, to determine a priming volume for de-priming processes according to various embodiments. The volume information may include dialysis machine holding volume information, dialyzer holding volume information, tubing information associated with tubing (for instance, patient line tubing, extracorporeal circuit) used to deliver fluid from dialysis machine 170 to a patient, patient extravasation rate, vascular refilling rate, and/or the like. In general, volume information may include any information that may be used to determine a volume of fluid that may be arranged within tubing 176, for instance, when primed (for example, in the absence of air within the tubing). Non-limiting examples of tubing information 550 may include tube length, tube inner diameter, tube outer diameter, tube material, tube compliance (for instance, amount of flexing under pressure), tube volume calculations, tubing tolerances, and/or the like. In some embodiments, tubing 176 may be or may form part of an extracorporeal circuit. Dialysis machine holding volume information may include the volume of fluid that may be held within dialysis machine 170 and/or components thereof (for instance, hubs, filter devices, and/or the like), such as a priming fluid during a priming phase. In general, dialysis information 132 may include a measurement, approximation, and/or the like of a priming volume, which may indicate the volume of priming fluid infused into the patient. Dialyzer holding volume information may include the volume of fluid that may be held within a dialyzer and/or components thereof of dialysis machine 170.

In some embodiments, de-priming logic 124 may determine at least a portion of the volume information based on operator input. For example, an operator may input certain tubing characteristics, such as tube length, diameter, feature set information, and/or the like. In other embodiments, an operator may input a tubing identifier (for instance, a manufacturer product identifier) and the de-priming logic may determine at least a portion of the tubing information based on available data associated with the tubing identifier (for instance, via a manufacturer database, an operator database, and/or the like). In a further example, an operator may create predefined configurations that may be selected that include predefined information defining tubing information. In a further example, dialysis machine 170 may be operative to automatically determine the type of tubing set, for instance, by reading or scanning a tag or identifier on the tubing or otherwise obtaining information about the tubing set. Embodiments are not limited in this context Blood characteristic information 134 may include values of measured blood characteristics. In general, blood characteristics may include any property of blood capable of being measured and/or calculated based on a measurement. Non-limiting examples of blood characteristics may include hematocrit, Hgb, BV, RBV, ABV, oxygen saturation, blood flow rate, and/or the like.

In various embodiments, dialysis logic 122, for example, via dialysis application 136, may operate to perform a dialysis process on a patient via dialysis machine 170, such as an HD treatment. For example, dialysis logic 122 may receive dialysis treatment information, such as patient characteristics, dialysis prescription information, and/or the like to perform a dialysis process on a patient. In some embodiments, dialysis logic 122, automatically or at least partially with manual intervention, may perform a priming phase of dialysis machine 170 and/or tubing 176. The priming phase may infuse a priming system fluidically coupled to dialysis machine 170, for instance, via tubing, with a priming volume of priming fluid. In some embodiments, the priming fluid may include saline and/or other fluids used to prime dialysis systems known in the art. In some embodiments, dialysis logic 122 may generate and/or provide a signal indicating the start and/or end of the priming process. In other embodiments, dialysis logic 122 may generate and/or provide information indicating and/or that may be used to determine the priming volume.

De-priming logic 124 may operate to perform a de-priming process according to some embodiments. A de-priming process according to various embodiments may operate to remove or substantially remove the volume of priming fluid from a patient and associated components (for instance, tubing 176, dialysis machine 170, extracorporeal circuit, and/or the like) within a de-priming time period. In some embodiments, de-priming logic 124 may initiate the de-priming process by setting the UFR of infusion pump 172 to a de-priming UFR for a de-priming time period.

The priming volume may be determined by de-priming logic 124 according to various embodiments. An illustrative priming volume may be about 240 milliliters (ml). In various embodiments, the priming volume may be about 50 ml, about 100 ml, about 150 ml, about 200 ml, about 250 ml, about 300 ml, about 350 ml, about 400 ml, about 500 ml, and/or any value or range of values between any of these values (including endpoints).

In some embodiments, the volume of priming fluid may be a known volume, for instance, in which the priming process operates to infuse the patient with a specified volume (for instance, about 240 ml). In another embodiment, the volume of priming fluid may be input by a user into dialysis machine 170, computing device 110, network node 152a-n, and/or the like. In additional embodiments, the volume of priming fluid may be determined based on the characteristics of dialysis machine 170, components of dialysis machine 170 (for instance, filters, internal conduits, and/or the like), and/or components associated with dialysis machine 170, such as tubing 176. Non-limiting examples of values that may be used to determine the volume of priming fluid may include a tubing volume, a dialysis machine volume, a tubing volume, an extracorporeal circuit volume, a volume of non-primed components (for instance, the dialysis machine volume may include a filter that is not primed), an accuracy adjustment, an error adjustment, a loss or migration adjustment (for instance, a calculated or estimated value of priming fluid that migrates beyond the vascular compartment that may not be subject to UF), patient extravasation rate, vascular refilling rate, and/or the like. In general, accuracy/error adjustment information may include information indicating the inaccuracy (for instance, tolerance, deviations, errors, patient extravasation rate, vascular refilling rate, and/or the like) or adjustments of fluid volume measurements associated with the dialysis machine 170, tubing 176, components thereof, and/or the like.

For example, the volume of priming fluid may be determined according to: volume of priming fluid=tubing volume+dialysis machine volume. In some embodiments, the dialysis machine volume may be a volume of a dialyzer of the dialysis machine. In another example, the volume of priming fluid may be determined according to the following: volume of priming fluid=(tubing volume+dialysis machine (i.e., dialyzer) volume)−volume of non-primed components. In some embodiments, the volume of priming fluid may be determined taking measurement errors or accuracy adjustments into account. Embodiments are not limited in this context.

In some embodiments, the priming volume to be removed from the patient does not necessarily equal the amount of priming fluid infused into the patient. Additional considerations (for example, patient factors and/or fluid volume factors) may be taken into consideration, such as vascular refill rate (measured or estimated), surrogates of vascular refill rate (such as patient position and time course of changes in patient position), rate of priming fluid infusion into the patient, priming fluid half-life in the patients vasculature, duration of de-priming procedure, time between start of de-priming procedure and Hgb measurement, combinations of any of the foregoing, and/or the like. Accordingly, the priming volume may be determined according to: priming volume=volume of priming fluid+/−patient factors. For example, the amount of fluid lost due to the vascular refill rate may be determined and subtracted from the volume of priming fluid to determine the priming volume. Embodiments are not limited in this context.

De-priming logic 124 may operate to set a UFR to a de-priming UFR to initiate the de-priming process. In various embodiments, the de-priming UFR may be set to remove the priming volume from the priming system (for instance, an extracorporeal circuit) within a de-priming time period. The de-priming UFR may be greater than the prescribed UFR(s) for patient treatment. For example, the de-priming UFR may be about 3000 ml/hour. In various embodiments, the de-priming UFR may be about 100 ml/hour, about 200 ml/hour, about 300 ml/hour, about 400 ml/hour, 500 ml/hour, about 1000 ml/hour, about 1500 ml/hour, about 2000 ml/hour, about 2500 ml/hour, about 3000 ml/hour, about 3500 ml/hour, about 4000 ml/hour, about 5000 ml/hour, about 6000 ml/hour, and/or any value or range of values between any of these values (including endpoints).

The de-priming time period may be set as a time short enough to complete the de-priming process within a time frame that avoids or reduces priming fluid trapping, priming fluid leakage beyond vascular compartment, and/or the like, while being long enough to avoid a UFR, blood flow rate, and/or extracorporeal hemoconcentration that may be harmful to the patient or otherwise undesirable. In some embodiments, the de-priming time period may be about 1-2 minutes (min). In other embodiments, the de-priming time period may be about 8 min. In various embodiments, the de-priming time period may be about 1 min, about 2 min, about 3 min, about 4 min, about 5 min, about 6 min, about 7 min, about 8 min, about 9 min, about 10 min, about 12 min, about 15 min, about 20 min, and/or any value or range of values between any of these values (including endpoints).

In some embodiments, de-priming logic 124 may determine the de-priming UFR and/or the de-priming time period based on various de-priming factors, such as RBV, priming volume, patient health characteristics, time since end of priming phase, rate and/or duration of priming fluid infusion, and/or the like. For example, de-priming logic 124 may determine (for instance, from predetermined information, experimental information, and/or the like) the time required for certain de-priming factors. For instance, a first period of time of A is required for an RBV of B; a second time period of C is required for a priming volume of D; a second time period E is required for patient health characteristic F; and so on. De-priming logic 124 may add up the time periods determined based on the de-priming factors (i.e., A+C+E)

and any other built-in time periods to determine the de-priming time period. Embodiments are not limited in this context.

In some embodiments, de-priming logic 124 may start the de-priming process based on one or more de-priming initiation factors. For example, in some embodiments, a de-priming initiation factor may be a specific start signal provided manually by a user via dialysis machine 170, computing device 110, and/or network node 152a-n. In other embodiments, the start signal may be provided automatically, such as by dialysis logic 122 responsive to various stages of the priming process including, without limitation, completion of the priming process, a time period during the priming process (for instance, X min after start of priming process), a time period after completion of the priming process, a time period after starting the dialysis process, an event (for instance, infusion of X ml of priming fluid), combinations thereof, and/or the like. In other embodiments, de-priming logic 124 may otherwise detect that the priming process has been completed or any other stage of the priming process. In some embodiments, de-priming logic 124 may start the de-priming process at a time period after the start of dialysis, such as 1 min, 2 min, 3 min, 4 min, 5 min, 10 min, 15 min, 20 min, 25 min, 30 min, and/or any value or range of values between any of these values (including endpoints) after the start of dialysis. For example, de-priming logic 124 may determine or otherwise receive information indicating how long after the start of the dialysis process patient priming will have completed, and use this information to determine a start time for the de-priming process.

In general, the de-priming process may be started within 1-2 minutes or otherwise as soon as possible after the initiation of the priming phase because the longer the duration from the beginning of the priming phase the more fluid may have migrated from the vasculature. For example, if the de-priming process is started 20 minutes after the priming phase, the actual volume of priming fluid to be removed from the patient's vasculature will be largely unknown as the rates of priming fluid extravasation, vascular refill, etc. are not quantified.

Accordingly, the de-priming process may be operated to start at a start time, at a de-priming UFR, and/or for a de-priming time period. For example, a de-priming process may operate at 3000 ml/hour for 8 minutes, then return the UFR to a prescribed UFR. In various embodiments, the de-priming process may be operated to maintain a blood flow rate at a target blood flow rate, for example, a blood flow rate below a high threshold and/or between a low threshold and a high threshold. For example, the de-priming UFR and/or de-priming time period may be selected to maintain a target blood flow rate below about 200 ml/min. In another example, the target blood flow rate may be between about 150 ml/min and 250 ml/min. In various embodiments, the target blood flow rate may be above about 100 ml/min, about 150 ml/min, about 200 ml/min, about 250 ml/min, about 300 ml/min, about 350 ml/min, about 400 ml/min, about 450 ml/min, about 500 ml/min, and/or any value or range of values between any of these values (including endpoints).

In various embodiments, blood characteristic measurement logic 126 may operate to measure, calculate, or otherwise determine at least one blood characteristic of a patient fluidically coupled to dialysis machine 170. In some embodiments, blood characteristic logic 126 may determine when the end of the de-priming process has occurred and, therefore, the patient blood has been de-primed. Accordingly, blood characteristic logic 126 may measure patient blood characteristics using de-primed blood. In some embodiments, blood characteristic logic 126 may measure blood characteristics in primed, hemodiluted blood and de-primed blood, indicating the condition of the blood at the time of measurement. For example, blood characteristic logic 126 may take a measurement at time X before or during the de-priming process (and, therefore, using hemodiluted blood) and at time X+n, after the de-priming process (and, therefore, using de-primed blood). In this manner, a healthcare professional may review the difference between the value in hemodiluted blood and de-primed blood.

Figure 2:
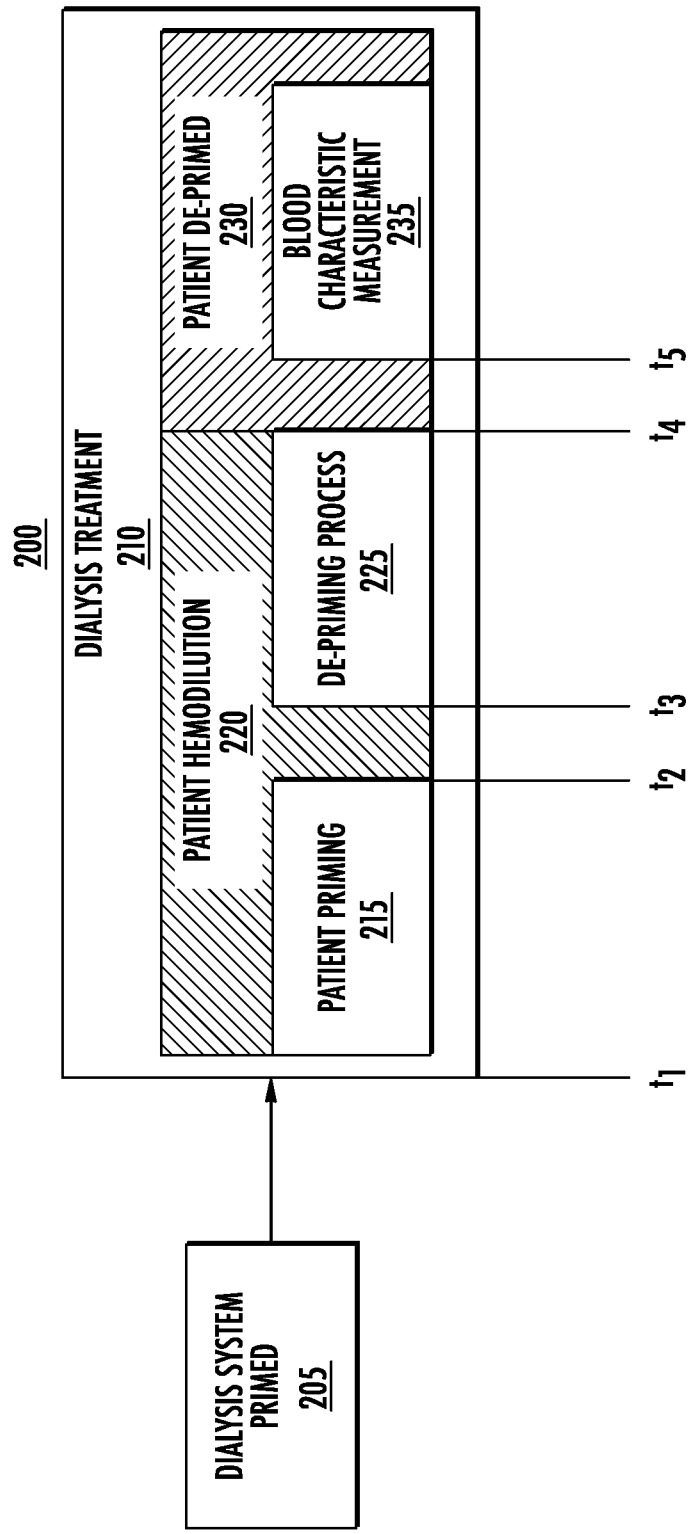
FIG. 2 illustrates a second exemplary operating environment in accordance with the present disclosure.

FIG. 2 illustrates an example of an operating environment 200 that may be representative of some embodiments. As shown in FIG. 2, operating environment 200 depicts a process diagram for a de-priming process according to some embodiments.

A dialysis system may be primed 205 and fluidically connected to a patient. A dialysis treatment 210 may start at $t_1$ infusing the patient with the priming fluid during patient priming 215, causing hemodilution 220 of the patient blood. At $t_2$, patient priming 215 has completed and a de-priming process 225 may be initiated at $t_3$. In some embodiments, $t_2$ and/or $t_3$ may be a specific time period after the start of dialysis, such as about 1 min to about 4 min after $t_1$. At $t_4$, de-priming process 225 has completed and the patient has been de-primed 230 of the priming fluid. For example, the duration between $t_3$ and $t_4$ may be a duration determined, estimated, or otherwise established that is sufficient to remove the priming volume from the priming system. Accordingly, a blood characteristic measurement 235 may be performed at $t_5$ measuring a blood characteristic of de-primed patient blood. In some embodiments, de-primed 230 may be or include a pre-dialysis approximation period of time where the de-primed patient blood is similar or substantially similar to the patient pre-dialysis blood (i.e., after de-priming, but before the effects of the dialysis treatment). The duration of de-primed 230 (i.e., the pre-dialysis approximation period) may be determined based on various factors and may have a duration of about 30 seconds to about 10 minutes (including values and/or ranges between any two of these values, including endpoints), for example, from the start and/or end of de-priming process 225. In some embodiments, de-priming logic 124 and/or blood characteristic measurement logic 126 may operate to determine the duration of de-primed 230 and take blood characteristic measurement 235 to determine pre-dialysis (a quasi-pre-dialysis or pre-dialysis approximation) measurement.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 3:
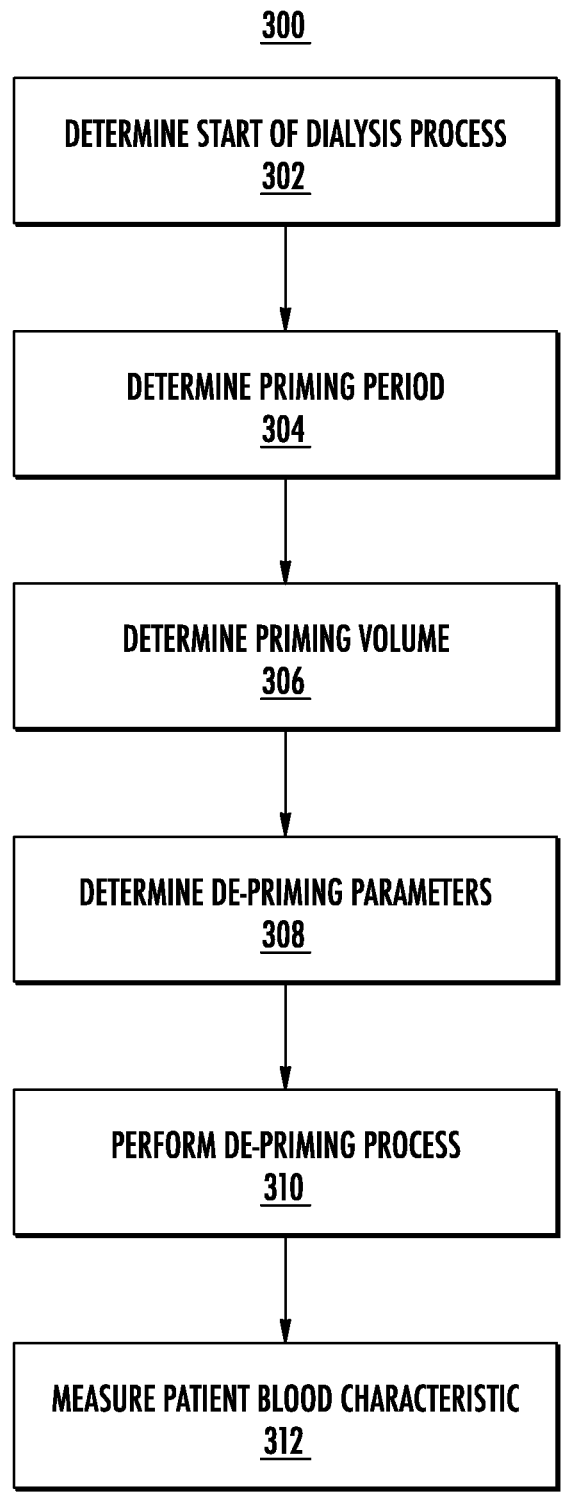
FIG. 3 illustrates a logic flow in accordance with the present disclosure.

FIG. 3 illustrates an embodiment of a logic flow 300 that may be representative of some or all of the operations executed by one or more embodiments described herein, such as computing device 110, dialysis machine 170, and/or components thereof. Logic flow 300 may be representative of some or all of the operations of executing a de-priming process according to some embodiments.

Logic flow 300 may determine the start of a dialysis process at block 302. For example, de-priming logic 124 may determine that a dialysis treatment of a patient has been started via dialysis machine 170. The patient may be fluidically coupled to dialysis machine 170 via tubing 176 (for instance, an extracorporeal circuit). At block 304, logic flow 300 may determine a priming period 304. For example, de-priming logic may determine how long it may take for the priming fluid arranged within dialysis machine 170, components thereof, and/or systems coupled thereto (for instance, patient monitoring devices 174a-n, tubing 176, and/or the like) that may be holding the priming fluid to infuse the patient with the priming fluid. At block 306, logic flow 300 may determine the priming fluid volume. For example, de-priming logic 124 may access, receive, calculate, or otherwise determine the priming volume to remove from the patient.

Logic flow 300 may determine de-priming parameters at block 308. Non-limiting examples of de-priming parameters may include a de-priming UFR, a de-priming UFG, a target blood flow rate (including, for example, upper and lower threshold bounds), a de-priming time period, a de-priming start time, and/or the like.

At block 310, logic flow 300 may perform the de-priming process. For example, de-priming logic 124 may set the UFR of ultrafiltration pump 172 to a de-priming UFR for a de-priming time period, then re-set the UFR to the previous, prescribed UFR. After completion of the de-priming process, logic flow 300 may measure a patient blood characteristic at block 312. In this manner, the patient blood characteristic, such as hematocrit and/or Hgb, may be measured using de-primed, non-diluted patient blood. In some embodiments, logic flow 300 may operate to administer a diagnosis and/or treatment, alone or in combination with a healthcare professional, based on the patient blood characteristic.

De-Priming Process Pilot Study: Estimation of Pre-Dialysis Hgb Concentration Using Intradialytic CLM Readings A pilot study of the de-priming process according to some embodiments was conducted in chronic HD patients. The patient population consisted of 27 patients (age 57.4±15 years, 70% males, 71% African-Americans) studied on up to three occasions and involving a total of (61) HD treatments.

Two pre-HD blood samples were drawn and measured in triplicate by Spectra East Laboratories (Rockleigh, N.J., United States of America), and the average used for comparison to CLM determined via a de-priming process according to some embodiments. Initial UFR was set to 3 L/hour for 8 minutes and then returned to the prescribed rate. Hgb was recorded continuously with the CLM. Differences of CLM to lab Hgb value is calculated as CLM reading at each time point minus averaged lab value.

Figure 4:
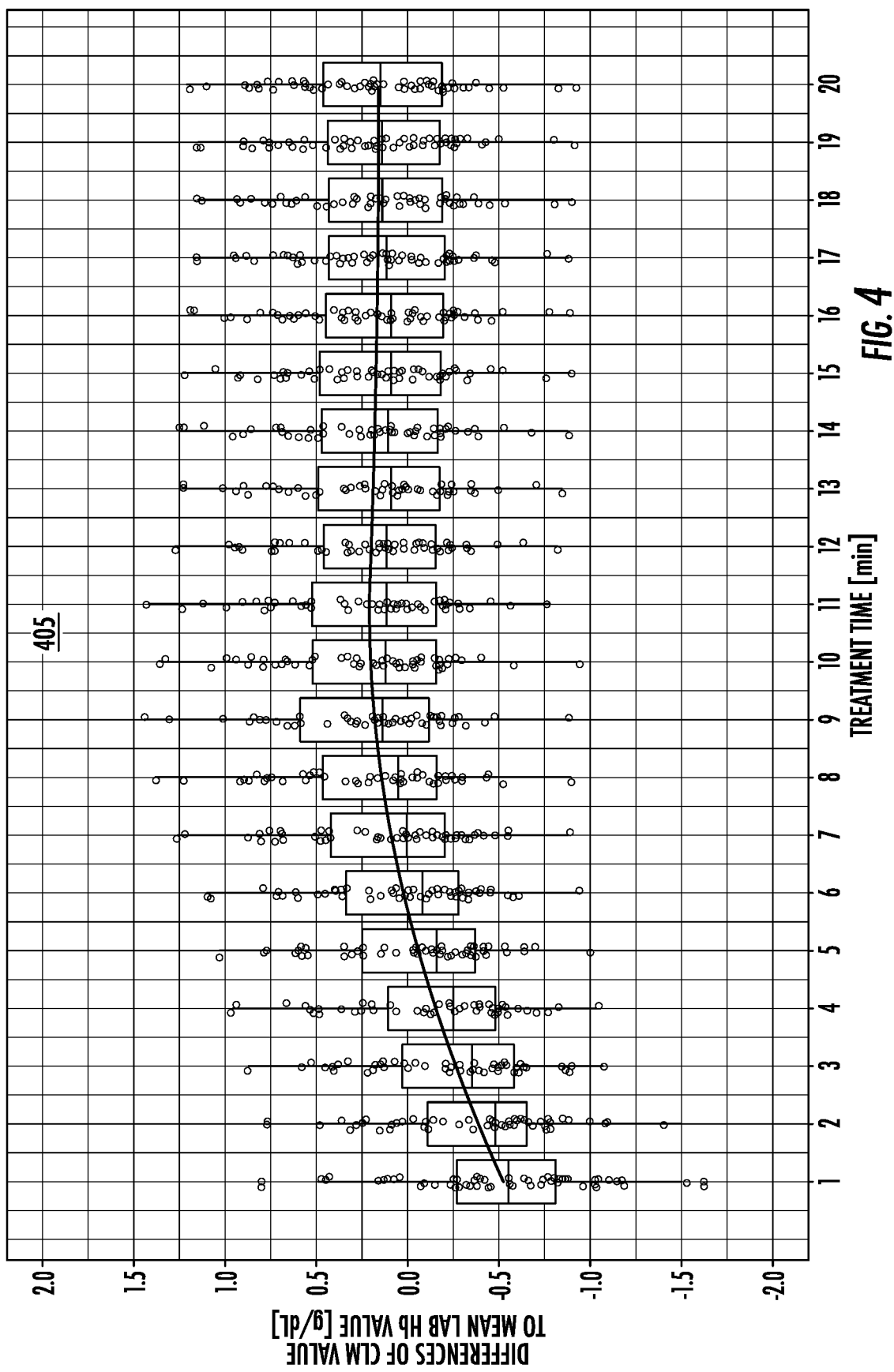
FIG. 4 illustrates a graph of results of differences between laboratory and intradialytic measurements of hemoglobin (Hgb) values of a de-priming process pilot study.
Figure 5:
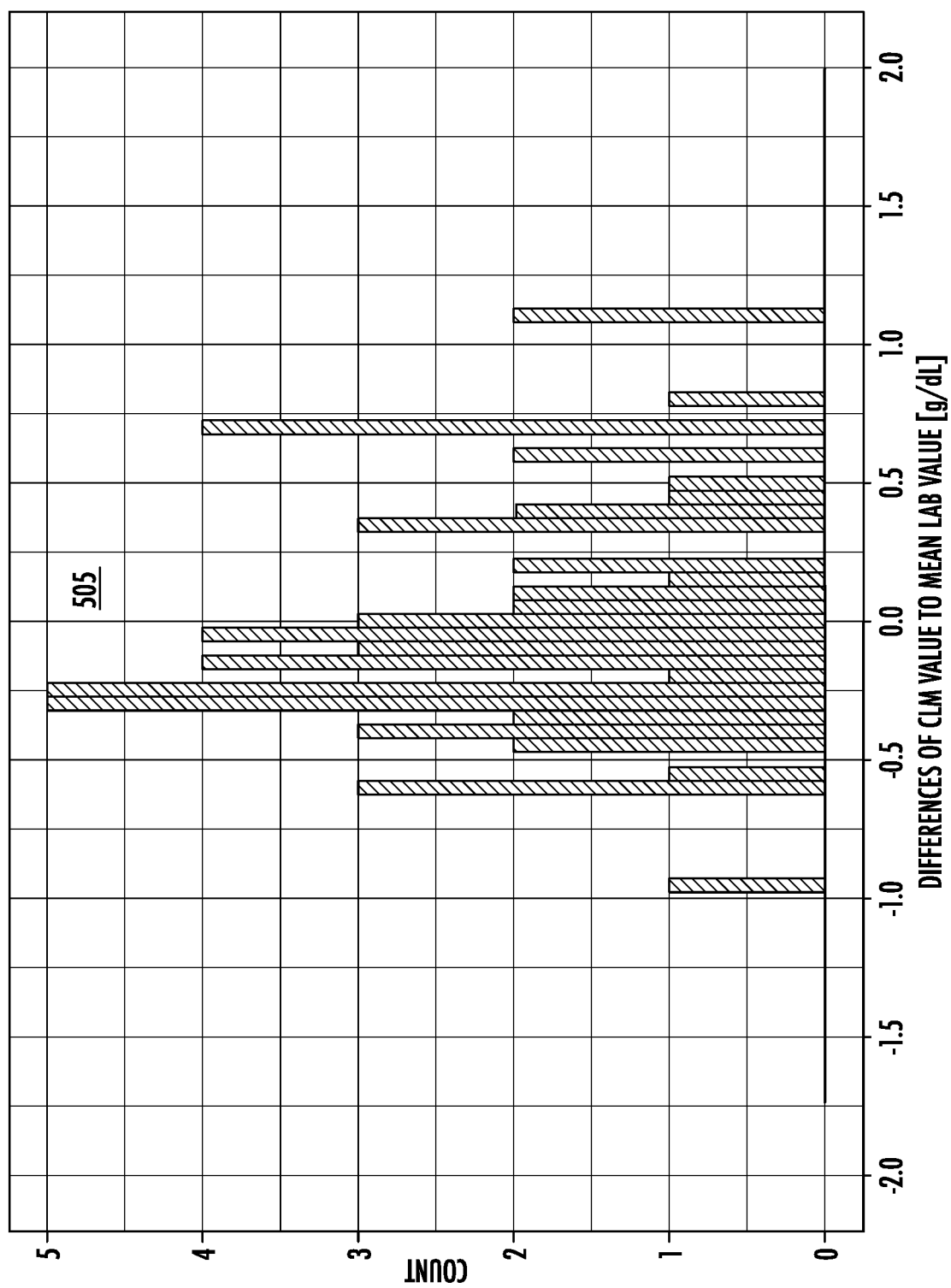
FIG. 5 illustrates a graph of results of a distribution of differences between real-time Hgb measurements and laboratory Hgb measurements of the de-priming process pilot study.

Along with fluid removal by rapid ultrafiltration via the de-priming process, the difference between CLM and lab value decreased and reached minimal at approximately 6 minutes (see graph 405 of FIG. 4), and about 75% of subjects had CLM Hgb values that were within ±0.5 g/dL of the corresponding laboratory reference Hgb (see graph 505 of FIG. 5). In general, FIG. 4 illustrates a graph 405 of results of differences between laboratory and real-time measurements of hemoglobin (Hgb) values of the de-priming process pilot study, and FIG. 5 illustrates a graph 505 of results of a distribution of differences between real-time Hgb measurements and laboratory Hgb measurements at the sixth minute of the de-priming process pilot study. Using a high initial UFR of 3,000 mL/hour, 75% of the CLM Hgb values were within ±0.5 g/dL difference of the corresponding averaged laboratory measurement at minute 6 into HD.

Figure 6:
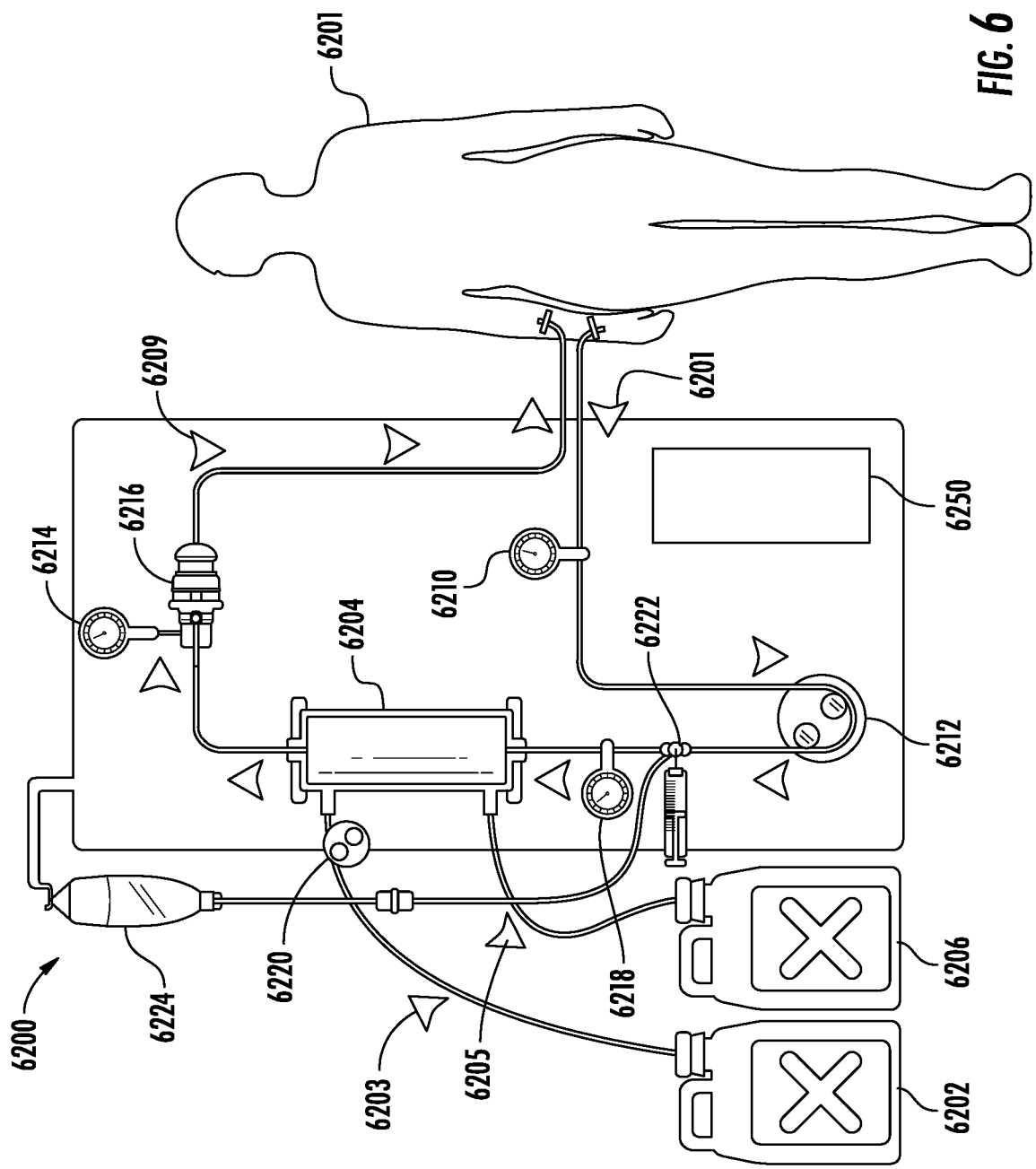
FIG. 6 illustrates an exemplary embodiment of a dialysis system configured in accordance with the present disclosure.

FIG. 6 illustrates a diagram of an exemplary embodiment of a dialysis system 600 in accordance with the present disclosure. Dialysis system 600 may be configured to provide hemodialysis (HD) treatment for a patient 601. Fluid reservoir 602 may deliver fresh dialysate to a dialyzer 604 via tubing 603, and reservoir 606 may receive spent dialysate once it has passed through dialyzer 604 via tubing 605. A hemodialysis operation may filter particulates and/or contaminates from a patient's blood through a patient external filtration device, for example, a dialyzer 604. As the dialysate is passed through dialyzer 604, unfiltered patient blood is also passed into dialyzer 604 via tubing 607 and filtered blood is returned to patient 601 via tubing 605. Arterial pressure may be monitored via pressure sensor 610, inflow pressure monitored via sensor 618, and venous pressure monitored via pressure sensor 614. An air trap and detector 616 may ensure that air is not introduced into patient blood as it is filtered and returned to patient 601. The flow of blood and the flow of dialysate may be controlled via respective pumps, including a blood pump 612 and a fluid pump 620. Heparin 622, a blood thinner, may be used in conjunction with saline 624 to ensure blood clots do not form or occlude blood flow through the system.

In some embodiments, dialysis system 600 may include a controller 650, which may be similar to computing device 110 and/or components thereof (for instance, processor circuitry 420). Controller 650 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. Controller 650 may also be operatively connected to and/or communicate with additional sensors or sensor systems, devices, and/or the like, although controller 650 may use any of the data available on the patient's biologic functions or other patient parameters. For example, controller 650 may send patient data to computing device 110 to perform processes according to some embodiments.

Figure 7:
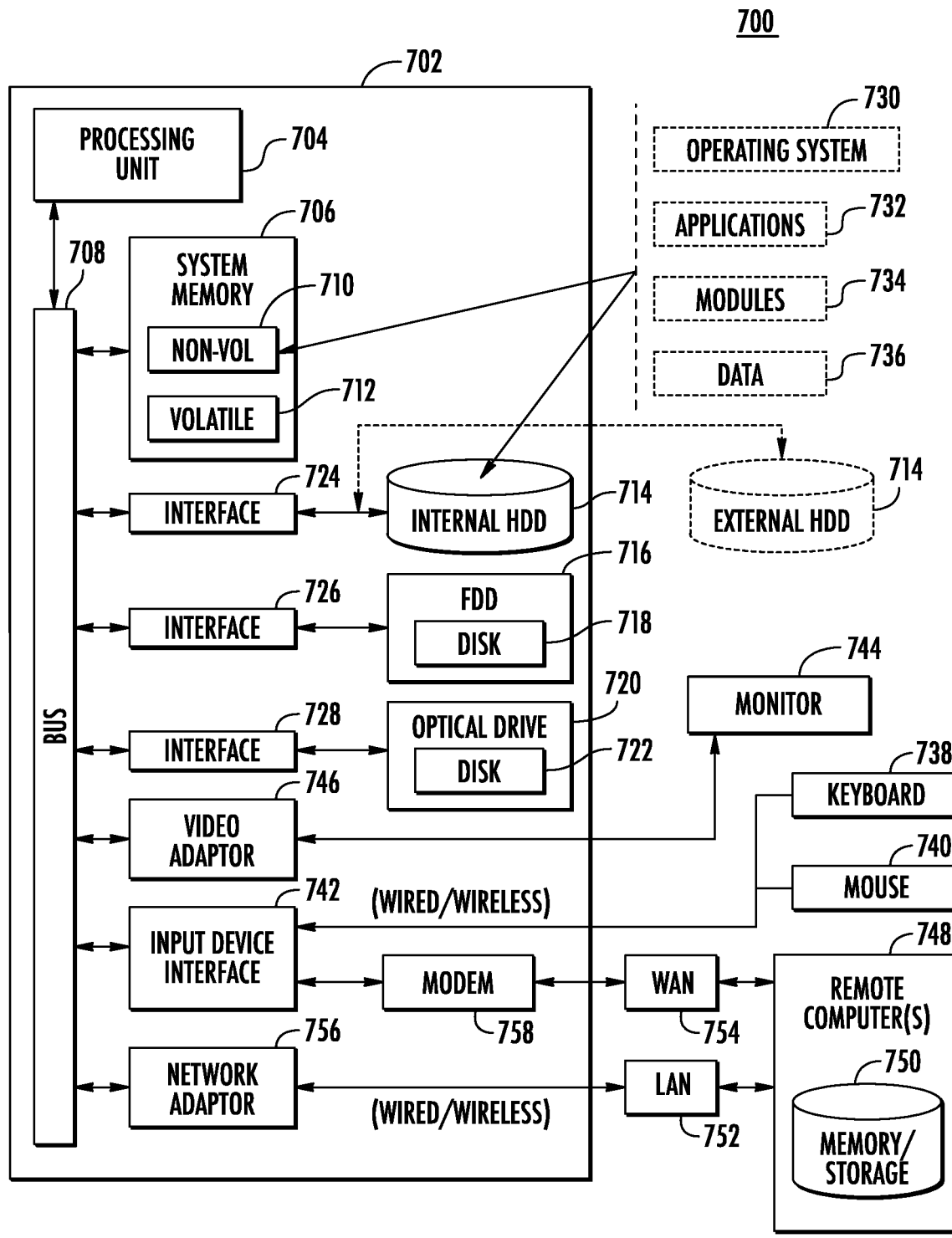
FIG. 7 illustrates an embodiment of a computing architecture in accordance with the present disclosure.

FIG. 7 illustrates an embodiment of an exemplary computing architecture 700 suitable for implementing various embodiments as previously described. In various embodiments, the computing architecture 700 may comprise or be implemented as part of an electronic device. In some embodiments, the computing architecture 700 may be representative, for example, of computing device 702 and/or components thereof. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 700. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 700 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 700.

As shown in FIG. 7, the computing architecture 700 comprises a processing unit 704, a system memory 706 and a system bus 708. The processing unit 704 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multiprocessor architectures may also be employed as the processing unit 704.

The system bus 708 provides an interface for system components including, but not limited to, the system memory 706 to the processing unit 704. The system bus 708 can be any of several types of bus structure that may further interconnect to a memory bus (with or without a memory controller), a peripheral bus, and a local bus using any of a variety of commercially available bus architectures. Interface adapters may connect to the system bus 708 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 706 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 7, the system memory 706 can include non-volatile memory 710 and/or volatile memory 712. A basic input/output system (BIOS) can be stored in the non-volatile memory 710.

The computer 702 may include various types of computer-readable storage media in the form of one or more lower speed memory units, including an internal (or external) hard disk drive (HDD) 714, a magnetic floppy disk drive (FDD) 716 to read from or write to a removable magnetic disk 718, and an optical disk drive 720 to read from or write to a removable optical disk 722 (e.g., a CD-ROM or DVD). The HDD 714, FDD 716 and optical disk drive 720 can be connected to the system bus 708 by a HDD interface 724, an FDD interface 726 and an optical drive interface 729, respectively. The HDD interface 724 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 710, 712, including an operating system 730, one or more application programs 732, other program modules 734, and program data 736. In one embodiment, the one or more application programs 732, other program modules 734, and program data 736 can include, for example, the various applications and/or components of computing device 110.

A user can enter commands and information into the computer 702 through one or more wire/wireless input devices, for example, a keyboard 738 and a pointing device, such as a mouse 740. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 704 through an input device interface 742 that is coupled to the system bus 708, but can be connected by other interfaces such as a parallel port, IEEE 994 serial port, a game port, a USB port, an IR interface, and so forth.

A monitor 744 or other type of display device is also connected to the system bus 708 via an interface, such as a video adaptor 746. The monitor 744 may be internal or external to the computer 702. In addition to the monitor 744, a computer typically includes other peripheral output devices, such as speakers, printers, and so forth.

The computer 702 may operate in a networked environment using logical connections via wire and/or wireless communications to one or more remote computers, such as a remote computer 749. The remote computer 749 can be a workstation, a server computer, a router, a personal computer, portable computer, microprocessor-based entertainment appliance, a peer device or other common network node, and typically includes many or all of the elements described relative to the computer 702, although, for purposes of brevity, only a memory/storage device 750 is illustrated. The logical connections depicted include wire/wireless connectivity to a local area network (LAN) 752 and/or larger networks, for example, a wide area network (WAN) 754. Such LAN and WAN networking environments are commonplace in offices and companies, and facilitate enterprise-wide computer networks, such as intranets, all of which may connect to a global communications network, for example, the Internet.

When used in a LAN networking environment, the computer 702 is connected to the LAN 752 through a wire and/or wireless communication network interface or adaptor 756. The adaptor 756 can facilitate wire and/or wireless communications to the LAN 752, which may also include a wireless access point disposed thereon for communicating with the wireless functionality of the adaptor 756.

When used in a WAN networking environment, the computer 702 can include a modem 758, or is connected to a communications server on the WAN 754, or has other means for establishing communications over the WAN 754, such as by way of the Internet. The modem 759, which can be internal or external and a wire and/or wireless device, connects to the system bus 708 via the input device interface 742. In a networked environment, program modules depicted relative to the computer 702, or portions thereof, can be stored in the remote memory/storage device 750. It will be appreciated that the network connections shown are exemplary and other means of establishing a communications link between the computers can be used.

The computer 702 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. An apparatus, comprising:
   at least one memory; and
   logic coupled to the at least one memory to perform a de-priming process of a patient undergoing a dialysis treatment via a dialysis machine operably coupled to the apparatus, the logic to:
   determine a priming volume of a primer fluid infused into a priming system associated with the patient during a priming phase of the dialysis treatment, cause an ultrafiltration rate of an ultrafiltration pump of the dialysis machine to be changed from a treatment ultrafiltration rate to a de-priming ultrafiltration rate to remove the priming volume over a de-priming time period, wherein the de-priming ultrafiltration rate is determined to remove the priming volume within the de-priming time period, and cause, after the de-priming time period, the ultrafiltration rate of the ultrafiltration pump to be changed back to the treatment ultrafiltration rate.

2. The apparatus of claim 1, the de-priming ultrafiltration rate comprising about 2000 ml/hour to about 4000 ml/hour.

3. The apparatus of claim 1, the de-priming time period comprising about 6 minutes to about 10 minutes.

4. The apparatus of claim 1, the de-priming ultrafiltration rate comprising about 3000 ml/hour and the de-priming time period comprising about 6 minutes.

5. The apparatus of claim 1, the logic to determine a de-priming start time for setting the ultrafiltration rate, the de-priming start time comprising a start time of the dialysis treatment.

6. The apparatus of claim 1, the logic to determine the priming volume based on a dialyzer volume and a tubing set volume.

7. The apparatus of claim 1, the logic to determine the de-priming ultrafiltration rate based on a target blood flow rate.

8. The apparatus of claim 7, the target blood flow rate comprising about 150 ml/min to about 250 ml/min.

9. A method of performing a de-priming process, the method comprising, via a processor of a computing device operably coupled to a dialysis machine performing a dialysis process on a patient:

determining a priming volume of a primer fluid infused into a priming system associated with the patient during a priming phase of the dialysis treatment;

causing an ultrafiltration rate of an ultrafiltration pump of the dialysis machine to be changed from a treatment ultrafiltration rate to a de-priming ultrafiltration rate to remove the priming volume over a de-priming time period, wherein the de-priming ultrafiltration rate is determined to remove the priming volume within the de-priming time period; and causing, after the de-priming time period, the ultrafiltration rate of the ultrafiltration pump to be changed back to the treatment ultrafiltration rate.

10. The method of claim 9, the de-priming ultrafiltration rate comprising about 2000 ml/hour to about 4000 ml/hour.

11. The method of claim 9, the de-priming time period comprising about 6 minutes to about 10 minutes.

12. The method of claim 9, the de-priming ultrafiltration rate comprising about 3000 ml/hour and the de-priming time period comprising about 6 minutes.

13. The method of claim 9, comprising determining a de-priming start time for setting the ultrafiltration rate, the de-priming start time comprising a start time of the dialysis treatment.

14. The method of claim 9, comprising determining the priming volume based on a dialysis machine volume and a tubing set volume.

15. The method of claim 9, comprising determining the de-priming ultrafiltration rate based on a target blood flow rate.

16. The method of claim 15, the target blood flow rate comprising about 150 ml/min to about 250 ml/min.

17. A method of performing a de-priming process, the method comprising, via a processor of a computing device operably coupled to a dialysis machine performing a dialysis process on a patient:

determining a priming volume of a primer fluid infused into a priming system associated with the patient during a priming phase of the dialysis treatment;

causing an ultrafiltration rate of an ultrafiltration pump of the dialysis machine to be changed from a treatment ultrafiltration rate to a de-priming ultrafiltration rate to remove the priming volume over a de-priming time period, wherein the de-priming ultrafiltration rate is about 2000 ml/hour to about 4000 ml/hour; and causing, after the de-priming time period, the ultrafiltration rate of the ultrafiltration pump to be changed back to the treatment ultrafiltration rate.

18. The method of claim 17, the de-priming time period comprising about 6 minutes to about 10 minutes.

19. The method of claim 17, comprising determining the priming volume based on a dialysis machine volume and a tubing set volume.

20. The method of claim 17, comprising determining the de-priming ultrafiltration rate based on a target blood flow rate.

21. A method of performing a de-priming process, the method comprising, via a processor of a computing device operably coupled to a dialysis machine performing a dialysis process on a patient:

determining a priming volume of a primer fluid infused into a priming system associated with the patient during a priming phase of the dialysis treatment;

causing an ultrafiltration rate of an ultrafiltration pump of the dialysis machine to be changed from a treatment ultrafiltration rate to a de-priming ultrafiltration rate to remove the priming volume over a de-priming time period, wherein the de-priming ultrafiltration rate is determined based on a target blood flow rate; and causing, after the de-priming time period, the ultrafiltration rate of the ultrafiltration pump to be changed back to the treatment ultrafiltration rate.

22. The method of claim 21, the de-priming time period comprising about 6 minutes to about 10 minutes.

23. The method of claim 21, comprising determining the priming volume based on a dialysis machine volume and a tubing set volume.

* * * * *